(12) United States Patent
Sachs et al.

(10) Patent No.: US 9,958,552 B1
(45) Date of Patent: May 1, 2018

(54) SYSTEMS AND METHODS FOR ROTATION BASED RECONSTRUCTION FOR MULTI-COLUMN DETECTOR GEOMETRIES

(71) Applicant: General Electric Company, Schenectady, NY (US)

(72) Inventors: Jonathan Benjamin Sachs, Haifa (IL); Yariv Grobshtein, Haifa (IL)

(73) Assignee: General Electric Company, Schenectady, NY (US)

( * ) Notice: Subject to any disclaimer, the term of this patent is extended or adjusted under 35 U.S.C. 154(b) by 0 days. days.

(21) Appl. No.: 15/639,650

(22) Filed: Jun. 30, 2017

(51) Int. Cl.
*G01T 1/00* (2006.01)
*G01T 1/17* (2006.01)
*A61B 6/00* (2006.01)

(52) U.S. Cl.
CPC .............. *G01T 1/17* (2013.01); *A61B 6/4233* (2013.01); *A61B 6/4435* (2013.01); *A61B 6/5205* (2013.01)

(58) Field of Classification Search
CPC ............. G01T 7/30; G01T 2207/10081; G01T 2207/10104; G01T 2207/30048; G01T 2207/30061
See application file for complete search history.

(56) References Cited

U.S. PATENT DOCUMENTS

| | | | | |
|---|---|---|---|---|
| 5,414,623 A | * | 5/1995 | Lu | .......................... G06T 11/006 |
| | | | | 382/131 |
| 2004/0131142 A1 | * | 7/2004 | Bruder | .................... A61B 6/032 |
| | | | | 378/19 |
| 2009/0110256 A1 | * | 4/2009 | Thielemans | ........... A61B 6/032 |
| | | | | 382/131 |

* cited by examiner

*Primary Examiner* — Kiho Kim
(74) *Attorney, Agent, or Firm* — Dean D. Small; The Small Patent Law Group, LLC

(57) ABSTRACT

A radiation detector system is provided that includes plural detector units and at least one processor. The detector units are configured to acquire imaging information at plural corresponding projection angles. The at least one processor is configured to acquire projections at the projection angles; organize the projections into groups based on the projection angles; and, for each group of projections, rotate a corresponding image from an original orientation so that the group of projections are parallel to a first axis of the rotated image, convolute and sum slices from the group of projections using kernels to provide a corresponding coordinate set forward projection; perform a back projection to provide back projections; and rotate the back projections to the original orientation and sum the rotated back projections to provide a back projected transaxial image.

20 Claims, 4 Drawing Sheets

SYSTEMS AND METHODS FOR ROTATION BASED RECONSTRUCTION FOR MULTI-COLUMN DETECTOR GEOMETRIES

BACKGROUND

The subject matter disclosed herein relates generally to medical imaging systems, and more particularly to imaging systems having multi-column detector geometries or arrangements.

In nuclear medicine (NM) imaging, such as single photon emission computed tomography (SPECT) or positron emission tomography (PET) imaging, radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

Multi-column detector systems may be used to provide a relatively large number of different views of the object. Iterative reconstruction algorithms may be used, for example, to provide improved image quality and/or support non-conventional system geometries. However, iterative algorithms generally require substantially more calculations than other approaches, resulting in the requirement of relatively large computational resources and/or relatively long reconstruction times. In particular, forward projection and back projection operations may contribute substantially to the required computational resources and/or reconstruction times.

BRIEF DESCRIPTION

In accordance with an embodiment, a radiation detector system is provided that includes plural detector units and at least one processor. The detector units are disposed about a bore configured to accept an object to be imaged. Each detector unit is configured to acquire imaging information at plural corresponding projection angles. The at least one processor is operably coupled to the detector units, and configured to acquire projections at the projection angles of the detector units; organize the projections into groups based on the projection angles; and, for each group of projections, rotate a corresponding image from an original orientation so that the group of projections are parallel to a first axis of the rotated image, convolute and sum slices from the projection group using kernels to provide a corresponding coordinate set forward projection; derive an error projection (e.g., divide the acquired projections by the projected estimated image to provide the error projection); perform a back projection (e.g., on the error projection) to provide back projections; and rotate the back projections to the original orientation and sum the rotated back projections to provide a back projected transaxial image (e.g., of terms used to update the estimated transaxial image).

In accordance with another embodiment, a method is provided that includes acquiring projections of imaging information at plural projection angles via plural detector units disposed about a bore configured to accept an object to be imaged. The method also includes organizing the projections into groups based on the projection angles. Also, the method includes, for each group of projections, rotating a corresponding image from an original orientation so that the group of projections are parallel to a first axis of the rotated image, convoluting and summing slices from the group of projections using kernels to provide a corresponding coordinate set forward projection, derive an error projection (e.g., divide the acquired projections by the projected estimated image to provide the error projection), performing a back projection (e.g. on the error projection) to provide back projections, and rotating the back projections to the original orientation and summing the rotated back projections to provide a back projected transaxial image (e.g., of terms used to update the estimated transaxial image).

DETAILED DESCRIPTION

Figure 1:
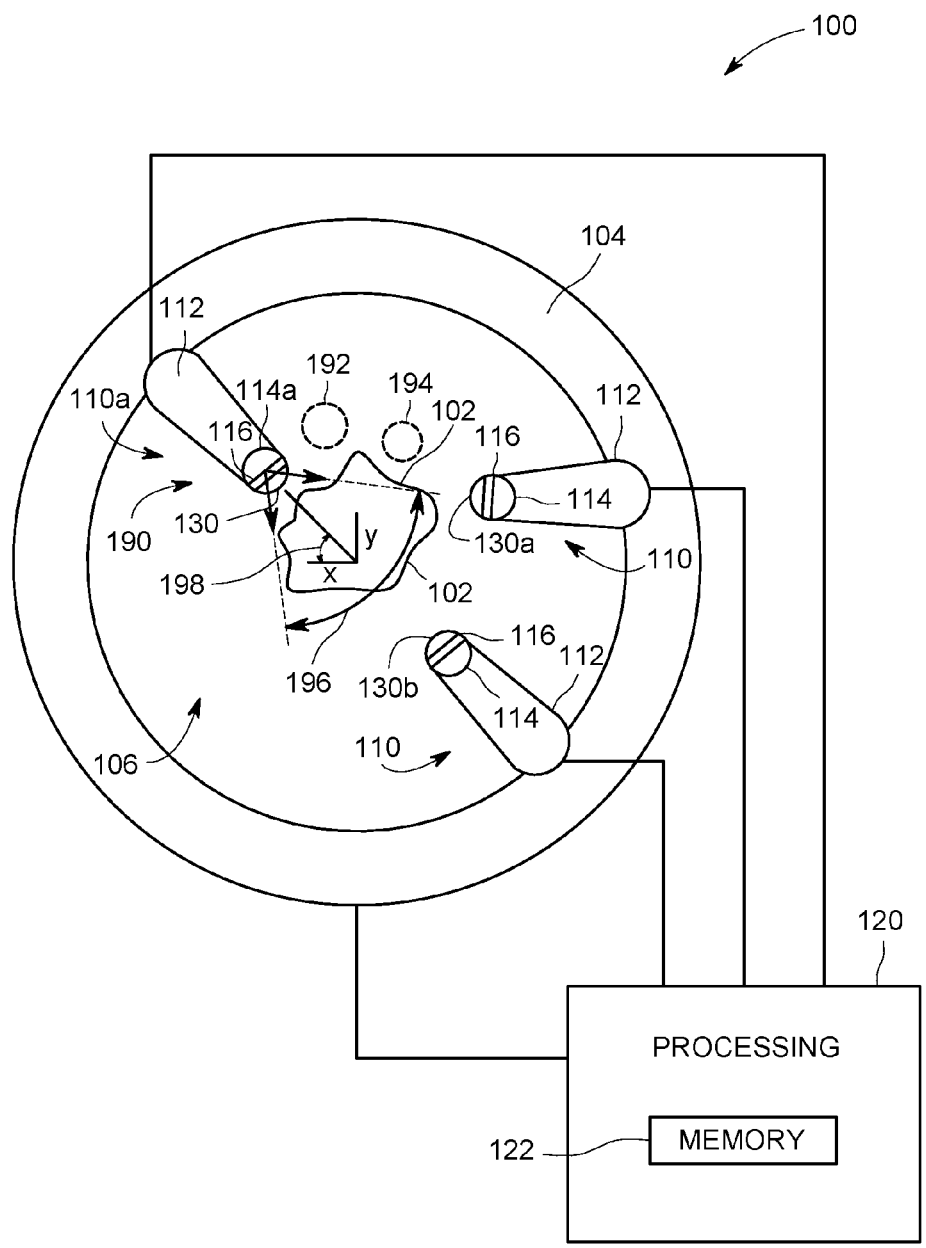
FIG. 1 provides a schematic view of a radiation detector assembly according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for improving computational efficiency for multi-column detector systems (e.g., system in which detector head can pivot or sweep with respect to a column) while still accurately modeling the system and providing desired image quality.

A technical effect of at least one embodiment includes improved image quality (e.g., due to accurate system modeling). A technical effect of at least one embodiment includes reduced computational resources and/or reduced reconstruction time.

Various embodiments relate to and/or utilize reconstruction algorithms. It may be noted that a reconstruction algorithm may be composed of forward projection and back projection operations, as well as other operations that are performed before, after, and/or in between the forward and back projection operations, such as a calculation of an error projection, a calculation of an update term, or a calculation of a scaling term, as examples.

FIG. 1 provides a schematic view of a radiation detector system 100 in accordance with various embodiments. As seen in FIG. 1, the radiation detector system 100 includes plural detector units 110 and a processing unit 120 that is operably coupled to the detector units 110. Generally, the detector units 110 are configured to acquire imaging information of an object 102 being imaged, and the processing unit 120 is configured to use the imaging information to reconstruct an image of the object 102, for example using an iterative process using a series of forward and back projections. The processing unit 120 may also be configured in various embodiments to control the detector units 110 to acquire the imaging information.

In the illustrated embodiment, the detector units 110 are configured to acquire emissions or radiation from the object 102. For example, the object 102 may be a human patient (or portion thereof) that has been administered a radiopharmaceutical, with the detector units 110 acquiring or detecting resulting radiation emissions from the object 102. In the illustrated embodiment, the detector units are mounted to a gantry 104 that is disposed about a bore 106. The bore 106 is configured to accept the object 102 for imaging, and the gantry 104 rotates about the bore 106. As seen in FIG. 1, for the illustrated embodiment, each detector unit 110 is mounted to the gantry 104 and accordingly rotates with the gantry 104. The detector units 110 may be configured for use with, for example, nuclear medicine (NM) imaging systems, positron emission tomography (PET) imaging systems, and/or single photon emission computed tomography (SPECT) imaging systems.

In the depicted embodiment, each detector unit 110 is arranged as a column extending radially inward from the gantry 104 toward the bore 106. As seen in FIG. 1, each detector unit 110 includes an arm 112 and a head 114. The arm 112 extends radially between the gantry 104 and the head 114. Further, the arm 112 may be configured to provide articulation of the head 114 along a radial direction (e.g., toward the object 102 or away from the object 102). Each head 114 includes a detector 116 and a collimator 130. The detector 116 may be a semiconductor detector configured to generate electrical signals responsive to received radiation. In some embodiments, the detector 116 may be a pixelated detector, or have a surface that is divided into a grid of pixels used to identify the location of received radiation. Generally, the collimator 130 is interposed between the detector 116 and the object 102 and is configured to control or limit the ranges of angles from which radiation may be received by the detector 116.

As the gantry 104 rotates about the bore 106, the detector units 110 rotate with the gantry about the bore 106 to additional positions at which imaging information may be acquired. For example, detector head 114a may begin at an original position 190 to acquire imaging information, then be rotated (along with gantry 104 and detector unit 110a) to position 192 (shown in dashed lines) to acquire additional imaging information, and then be rotated again to position 194 to acquire further additional imaging information. At each rotational position of the gantry 104, the viewing angle of each corresponding detector unit 110 changes, providing additional viewpoints from which to view the object 102. Also, each detector head 114 is configured to sweep or pivot with respect to arm 112 over a sweep range 196 providing an even larger number of viewing or projection angles. One example of a projection angle 198 (shown relative to x and y axes) is shown in FIG. 1; however it may be noted that the combination of a number of available rotational positions along with a number of available angles over a sweep range provides a relatively large number of available viewing or projection angles. Accordingly, each detector unit 110 is configured to acquire imaging information at plural corresponding projection angles. Also, it may be noted that, while only three detector units 110 are shown in FIG. 1 for ease and clarity of illustration, a different number of detector units 110 may be used. As just one example, a larger number of detector units 110 (e.g., 12) may be evenly distributed about the circumference of the gantry 104.

The processing unit 120 is operably coupled to the detector units 110, and is configured to receive imaging information (e.g., signals generated responsive to absorption of photons with the detectors 116) from the detector units 110. The processing unit 120 may also be configured to provide control signals to the gantry 104 and/or detector units 110. The depicted processing unit 120 uses the received imaging information from the detector units to reconstruct an image employing a technique that uses forward projection and back projection. In various embodiments, the processing unit 120 may utilize an iterative technique (e.g., maximum likelihood expectation maximization method (MLEM)) to reconstruct an image. For example, as part of an MLEM, the processing unit 120 may read projections acquired by the detector units 110, as well as system parameters (e.g., physical properties of the system, including physical properties of the detectors 116 and collimators 130). The processing unit 120 may also read system models (e.g., kernels) that represent the probability distribution of counts from a voxel to a square pixelated detector, with the pixels registered to the voxel or shifted relative to the voxel. Then, the processing unit 120 may set an initial estimated image (e.g., with voxels equal to one). Next, the processing unit 120, for each iteration, may forward project the estimated image to provide a forward projection of the estimated image, derive an error projection (e.g., divide the acquired projections by the projected estimated image to provide the error projection), back project the error projection, and set a new estimated image based on the back projected error projection. The new estimated image may be subjected to one or more additional iterations.

However, it may be noted that, for the large number of available projection angles utilized with a multi-head detector (e.g., radiation detector system 100), use of conventional iterative approaches may be become cumbersome or impractical due to required computational resources. Accordingly, various embodiments provide for more efficient processing (e.g., by processing unit 120). Various embodiments group projections based on projection angle for separate processing (e.g., iterative forward projection and back projections are performed separately based on the groupings based on projection angle), and subsequently combine the results of the separate group-based processing to provide a final or diagnostic image.

For instance, the depicted processing unit 120 is configured to acquire projections at various projection angles of the detector units 110. For example, the processing unit 120 may control the gantry 104 and detector units 110 to acquire imaging information at one or more rotational positions of the gantry 104 and at various points throughout sweep ranges of the detector units 110. Acquired imaging information may be correlated with information identifying the projection angle at which the information was acquired (e.g., by knowing the particular detector, the rotational position of the gantry, and the portion of the sweep range at which the detector was positioned during acquisition of a portion of the imaging information, the projection angle for that portion of the imaging information may be determined). The processing unit 120 of the illustrated embodiment next organizes the projections into groups based on the projection angles. It may be noted that the projections may be grouped by particular angle, or may be grouped over a range of angles. For example, a range of angles may be used to group projections (e.g., X degrees +/−0.5 degrees).

Then, for each group of projections, the processing unit 120 may rotate an image corresponding to the particular group of projections (e.g., an image acquired with the group of projections, or an estimated image from a previous iteration) from an original orientation so that the group of projections are parallel to a first (e.g., X) axis of the rotated image. The forward and back projections may be performed using the rotated image. In some embodiments, for the forward projection, the image is rotated and then convolved and summed. For the back projection, first convolution and summing are performed for one angle (group), then the result is rotated (according to the specific group angle) and this result is summed to the final back projection result volume.

For example, in various embodiments, the processing unit 120 next organizes projections within the group based on a second (e.g., Y) axis coordinate to provide coordinate sets (e.g., Y coordinate sets). (It may be noted that the grouping to provide the coordinate sets may not be performed in various embodiments). The processing unit 120 next convolutes and sums slices from the group of projections (e.g., slices of each coordinate set) using kernels to provide a corresponding coordinate set forward projection. Next, the processing unit 120 performs a back projection to provide back projections. For example, after forward projection, an error projection may be calculated (e.g., a ratio between the measured projection and the forward projection), and a back projection is performed on the error projection. The processing unit 120 then sums and rotates the back projections to the original orientation to provide a back projected transaxial image. For example, the back projections may be rotated by the same magnitude of angle used for the initial rotation, but in an opposite direction, and then summed. For example, if a 45 degree clockwise rotation was used to orient the group of projections parallel to the X axis, the back projections may be rotated 45 degrees counter-clockwise. The back projected transaxial image may be used for subsequent iterations, represent the final image (e.g., an image used for diagnostic purposes by a practitioner). It may be noted that the back projection may be completed once all the groups (angles) are used, and then an image update (using the back projection result) may be performed. After the image update is performed, it is possible to stop, or to continue for more iterations.

Figure 3:
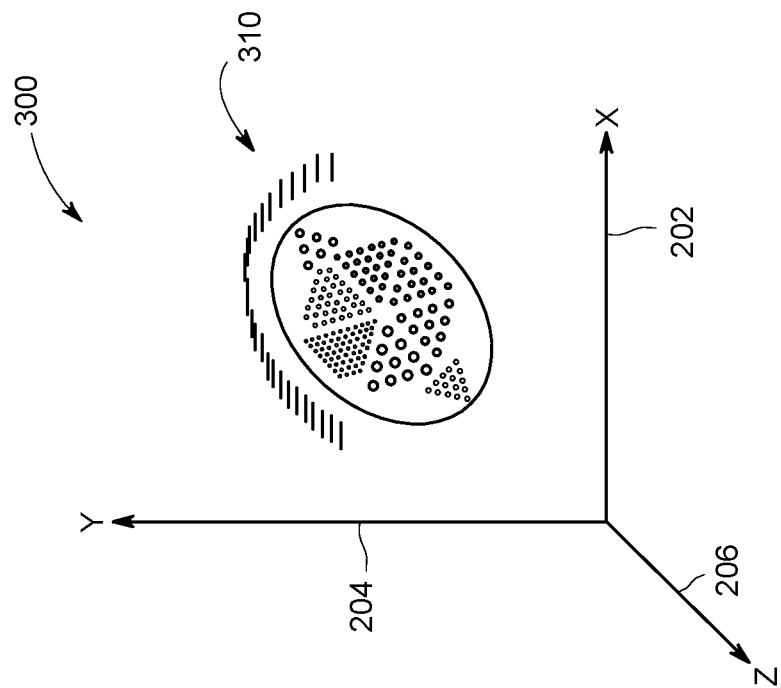
FIG. 3 shows an example of the image of FIG. 2 in a rotated orientation.
Figure 2:
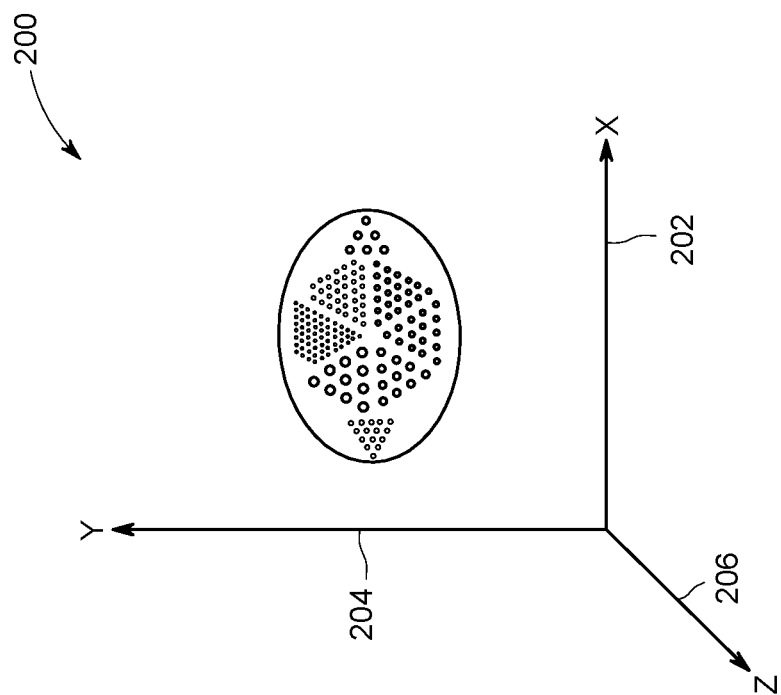
FIG. 2 illustrates an example of an image at an original orientation.

Accordingly, in various embodiments, the processing unit 120 may be understood as performing a forward projection and a back projection (or a series of forward and back projections). For example, the processing unit 120 may perform a forward projection algorithm as follows. First, projections may be grouped by projection angle. An example of a transaxial image 200 oriented along an x-axis 202, a y-axis 204, and a z-axis 206 is shown in FIG. 2, with the transaxial image 200 corresponding to a group of projections organized by projection angle. FIG. 2 may be understood as representing the image 200 in an image domain. For each group of projections, the resulting transaxial image is rotated so that the projections are parallel to the x-axis of the rotated image. FIG. 3 illustrates the transaxial image of FIG. 2 rotated to a new orientation 300, with the projections or detectors 310 parallel to the x-axis 202. In various embodiments, an attenuation correction factor may next be applied by the processing unit 120. Then, optionally, within each group, projections are organized by y coordinate. For example, projections may be grouped so that projections having the same distance (or within a predetermined range of distances) are grouped together. It may be noted that in other embodiments, each projection may be processed separately without Y coordinate grouping. The selection of whether or not to group by y coordinate (or other coordinate) may be made based on performance (e.g., which technique is expected to be faster, based on the data and processing hardware). Next, for each projection, xz slices are convoluted using kernels, and summed to provide a projection. The kernels may correspond to or represent system resolution. Then, forward projections are extracted. The extracted forward projections may be shifted (e.g., via a one dimensional kernel) from the derived projections. For example, the forward projections may be shifted to account for shifting between projection pixels and reconstructed object-space voxels caused by the sweeping of detectors.

After performing the forward projection, the processing unit 120 of the illustrated embodiment performs a back projection. As discussed elsewhere herein, additional calculations or steps may be performed between the forward and back projections, including calculation of an error projection. In various embodiments, the processing unit 120 may perform a back projection algorithm as follows. In some embodiments, the projections include error projections which are calculated based on the measured projections and the forward projecting of the last image estimate (e.g., by taking a ratio between the two). With projections grouped by projection angle, the processing unit 120, for each angle, groups projections by y coordinate (as discussed herein, the grouping by y coordinate is optional in various embodiments). Then, for each projection organized by y coordinate, the processing unit 120 may shift (e.g., to account for shifting between projection pixels and reconstructed object-space voxels caused by the sweeping of detectors) and assign each projection to an adjusted projection, which is a projection of xz dimension. Then the adjusted projections are convoluted and projected onto xz slices with kernels. Next, the processing unit 120 rotates and sums the image of xz slices to provide a back-projected transaxial image, which may be used for further iterations, or may be combined with back-projected transaxial images from other groups of projections for different projection angles to provide a final image. The rotation returns the back projection to the original orientation as seen in FIG. 2.

As discussed herein, in various embodiments the processing unit 120 is configured to apply a shift to register or align a projection with the object 102 being imaged. In various embodiments, the shift may be applied during a forward projection and/or a back projection. It may be noted that, for detectors that do not sweep or pivot but instead only rotate with a gantry, the pixels of the detector and voxels of an object being imaged may be inherently registered for a rotation-based reconstruction algorithm. If the detectors rotate around the system center of rotation (COR), while the object rotation in the algorithm rotates around the same point (e.g., a central point of the FOV that coincides with the COR), the pixels and voxels will be registered. However, in an arrangement including columns and detector heads that sweep or pivot about the columns (e.g., radiation detector system 100), the rotation of each head around its column center of rotation resulting from the sweeping or pivoting causes a shift or translation between the pixels of the projections and the reconstructed object-space voxels.

Accordingly, in various embodiments, the processing unit 120 applies a shift to register a projection with the object 102 being imaged. The shift may be applied in different manners in different embodiments. For example, in some embodiments, projection pixels are shifted. The shift may be achieved using various interpolation methods. As one example, a weighted average between 2 adjacent pixels may be employed. Such a weighted average may be implemented using a one-dimensional convolution. As another example, pre-computed shift kernels may be employed. In some embodiments, n sets of shifted kernels may be generated, where the shift step size is ps/n (where ps is pixel size), starting from shift=0 (registered) to shift=ps*(1−1/n). Generally, use of pre-computed shift kernels in various embodiments provides improved image quality; however, use of pre-computed shift kernels may consume additional processing resources relative to using an interpolation method.

As discussed herein, in various embodiments, the processing unit 120 is configured to apply an attenuation correction factor. It may be noted that the processing unit, in various embodiments, applies the attenuation correction factor as part of a forward projection and/or back projection. In various embodiments, the processing unit 120 is configured to determine attenuation correction parameter corresponding to an application time of the attenuation correction factor. It may be noted that, with present computational performance of typical processors, it is generally not feasible to use a ray tracing model to correct the attenuation of photons from each voxel of the object to each pixel of the detectors. It may also be noted that, for detector using parallel-hole collimators, attenuation may be modeled only for rays that are perpendicular to the detector. The timing of attenuation correction may be applied before or after a convolution, with a convolution performed during the forward projection and during the back projection. Accordingly, for each step, an attenuation correction may be performed under two options—post convolution (convolution is first performed and then attenuation correction), or pre convolution (convolution is performed after attenuation correction). As a result, when attenuation correction is performed during both a back projection and forward projection, there are four total options for the timing of performance of attenuation correction: (1) before both the forward and back projection convolutions, (2) after both the forward and back projection convolutions, (3) after the forward projection convolution and before the back projection convolution, and (4) before the forward projection convolution and after the back projection convolution. While each option may not necessarily reflect the true physics of the detection, the various options may be utilized to provide improved image quality. The particular option that works best varies by clinical task. Accordingly, a parameter for selecting which option of timing of application of attenuation correction factor(s) may be determined, with the appropriate value selected for each particular scan and corresponding reconstruction.

It may be noted that certain conventional Anger cameras enable the acquisition of projections with different pixel sizes to optimize the trade-off of noise and resolution in reconstructed images. However, pixelated detectors acquire data into a fixed pixel size defined by the discrete physical pixels of a detector. Accordingly, in various embodiments, the processing unit 120 is configured to modify a voxel size from an original size corresponding to a pixel size of the detector units 110.

The modification of voxel size (e.g., of a reconstructed image) may be performed using various techniques. For example, using a first technique, the original projections with a dimension of M×N pixels may be re-sized by summing "n" adjacent pixels pi of size s×s to generate a new projection with a dimension of (M/n)×(N/n) with pixels $newp_i$ of size ns×ns.

As another example, using a second technique, original projections may be used to reconstruct an image with voxel size of s×s×s. Then, after each update, a filter may be applied. For example, an intermediate low pass filter may be applied. The low pass filter may have a cutoff frequency (cf) of cf=$s_{orig}/s_{new}$, where $s_{orig}$ is the original voxel size and $s_{new}$ is the new voxel size. As another example, a Gaussian filter may be applied. The Gaussian filter may have a full width half maximum (FWHM) of $s_{new}/s_{orig}$. After application of the filter, the reconstructed image may be re-sampled into a voxel size of $s_{new} \times s_{new} \times s_{new}$.

As one more example, using a third technique, projections may be resized, and then the original kernels resized or new kernels generated for the appropriate pixels size. Then, an image may be reconstructed using the new projections and kernels.

As discussed herein, kernels may be used as part of a convolution process for forward and/or back projection. In various embodiments, the processing unit 120 is configured to use a first kernel for convolution in a first direction (e.g., x direction), and to use a second kernel for convolution in a second direction (e.g., z direction). For example, one 2D kernel may be used to convolve an image plan in the X and Z directions. However, the use of separable kernels (two 1-dimensional kernels—one applied in the x direction and the other in the z direction) may be used to accelerate the computations in various embodiments. It may be noted that rotation based reconstruction may use a convolution operator for forward and back projection. Use of such a convolution operator requires multiplying each voxel by a kernel having a dimension of N×M (or N*M multiplications). In various embodiments, use of separable kernels (or a first kernel for convolution in a first direction and a second kernel for convolution in a second direction) reduces the number of multiplications by a factor of (N*M)/(N+M). Accordingly, convolutions may be handled more efficiently (e.g., the processing unit 120 operates more efficiently using separable kernels as discussed herein). It may be noted that in some embodiments, the second kernel may be different than the first kernel. It may further be noted that, in some embodiments, the first and second two kernels in some embodiments may include the same data, but transposed (e.g., one kernel is a row vector and the other is a column vector, but the data elements in the two vectors are the same).

For example, in some embodiments, instead of a kernel K of dimension N×M, a kernel s and a kernel t may be used. The kernel s may be a row vector of dimension 1×M used to convolve an image over the x axis. Also, the kernel t may be a column vector of dimension N×1 to convolve the x-convolved image over the z axis. The kernels s and t in various embodiments are configured such that the Hadamard product of matrix S (N rows of s) and matrix T (M columns of t)~K. For example, as a first step, a first column of a 2D kernel K may be divided by a sum of the first column to provide vector d (where d=K(:,1)./sum(K(:,1)1)). As a second step, the first column of the 2D kernel K may be divided by a column vector of a sum of rows of K to provide vector e (where e=K(:,1)./sum(K,2)). As a third step, a Hadamard multiplication of the 2 vectors may be performed to provide f (where f=e.*d). As a fourth step, a square root of the first column may be divided by f, with g=sqrt(K(:,1)./f), and t=g.*d. K may be then be substituted with K' and steps 1 to 4 repeated to derive a transpose of s.

Additionally or alternatively, in various embodiments, the processing unit 120 may be configured to compensate for mechanical offsets from ideal system. Generally, accurate reconstruction requires knowledge of system geometry. Reconstruction algorithms typically make assumptions regarding the relationship of the detectors and the object space to simplify the algorithm used for forward and back projection of the images. For example, for rotational reconstruction algorithms, it may be assumed that the y axis of the detector is parallel to the z axis of the object space for all views. Such an assumption enables forward and back projection by simple rotation of the object around the z axis such that the x and y axes of the detector are parallel to x and z axes of the object, respectively. However, gamma cameras may be flawed by mechanical inaccuracies that can be quantified by calibration procedures, and these inaccuracies may accordingly be accounted for in the reconstruction. Mechanical inaccuracies in which the detector plane is parallel to the xz object plane may be compensated for, for example, by a two-dimensional translation and rotation of the projection such that the x and y axes of the detector are parallel to x and z axes of the object, respectively. Alternately, the object may be rotated and translated to achieve the alignment prior to forward and back projection. If the detector plane is not parallel to the xz object plane (e.g., due to sagging), additional axes of rotation may be applied, such that the x and y axes of the detector are parallel to the x and z axes of the object, respectively, and the relative position of the object to the detector is preserved prior to forward and back projection.

In some embodiments, the processing unit 120 is configured to partition the acquired projections into subsets, and to perform the forward and back projections (e.g., iteratively) based on the subsets. For example, to accelerate the reconstruction run-time, projection data may be portioned into subsets or blocks, and only part of the data used in each forward projection and back projection. Algorithms that use subsets include OS-EM, OS-GP, and BSREM. For certain conventional cameras, there is one projection per angle, and each subset is comprised of n projections which were acquired at n angles, with each projection covering the entire FOV of the object. However, due to multiple projections for each angle in multi-column systems and each projection covering a small portion of the FOV, applying the conventional subset partitioning techniques is not effective. Accordingly, in various embodiments, projections are grouped that are viewing the same angle (or range of angles). Each subset then includes several angle groups, with each angle group including all projections viewed at that angle. It may be noted that, while each projection may cover only a small part of the FOV, typically the group of projections in each angle group will jointly cover the entire FOV of the object. It may be noted that the number of views might not be equal among the different subsets. Each subset may be selected to have an equal number of angles. Accordingly, the angles may be understood as balanced and an entire angular range may be sampled.

It may also be noted that, in rotation based reconstruction algorithms, the object should generally be rotated for each acquired angle. However, as the number of angles is increased, the computing run-time is increased. For certain conventional cameras, the number of projection angles may be limited between 60 and 120. However, for multi-column based geometry, there may be many—even thousands—of views. Accordingly, various embodiments provide techniques for addressing computation time or processing requirements for multi-column detectors.

For example, in some embodiments, the processing unit 120 is configured to plan (e.g., plan movements of the detector units 110) image acquisition to provide a predetermined number of projection angles. For example, the predetermined number of projection angles may be set below a threshold. Accordingly, in various embodiments, the acquisition is planned to provide a relatively low number of unique angles, while still achieving good angular sampling and coverage. For example, the acquisition may be planned to include particular rotation steps (steps of rotation of the gantry 104) and sweep steps (pivoting of the detector head 114 relative to the arms 112) to provide a predetermined number of unique angles (e.g., 360 unique angles), even if there are thousands of views. Accordingly, the number of required object rotations during the reconstruction may be reduced.

Additionally or alternatively, angle binning may be performed during the reconstruction. For example, instead of using exact angles, several projections with different but relatively close angles may be grouped together, with the bin size (or allowed error) a specified parameter. For example, with a bin size of 1 degree (or a maximum error of +/−0.5 degrees), a maximum of 360 bins will be used, with a corresponding 360 rotation operations for the reconstruction. Generally, relatively smaller bin sizes will result in relatively better image quality but relatively larger computation requirements (e.g., longer run-times).

Further, it may be noted that, for rotation-based reconstruction, a depth-dependent kernel is used to model the collimator-detector response. The depth is the distance between the voxel and the collimator face. Typically, a set of kernels is generated for different distances across the required range. To keep the computing resources practical, conventionally the step size between adjacent kernels is the voxel size. However, because the detector may be located in any position over the range during the scan, a kernel with an accurate distance may not be available when using the voxel size as the step size. This inaccuracy may degrade image quality.

Accordingly, in various embodiments, the processing unit 120 is configured to adjust a kernel distance from an original distance corresponding to a voxel step size. Various methods may be employed in different embodiments to adjust the kernel distance. For example, kernels may be generated using a fine step size. In various embodiments, instead of kernels spaced on voxel apart, kernels may be generated using a smaller step size, such as $\frac{1}{8}$ or $\frac{1}{24}$ of voxel size.

As another example, kernels may be interpolated. In some embodiments, instead of choosing a kernel with a shortest distance to the actual voxel-collimator distance, an interpolation of the closest 2 kernels (one greater than the actual distance and one smaller than the actual distance) may be used. As one example, linear interpolation between the 2 kernels according to the distance ratio of each from the actual distance may be employed. In other embodiments, different interpolation methods may be employed. It may be noted that interpolation of kernel size may be utilized to improve accuracy while keeping memory resources relatively low, but may require more processing steps (e.g., relative to use of predetermined kernel distances having a fine step size). Accordingly, use of either fine step size or interpolation may be selected based on the available hardware platform. It may further be noted that in various embodiments, use of fine step sizes for kernels may be used in conjunction with interpolation.

As one more example, kernels may be generated on the fly. In some embodiments, the processing unit 120 may generate the kernel according to a known distance for each scan. After generation of the kernel, the kernel may be saved (e.g., in a memory) for use in subsequent iterations. It may be noted that each of the three methods of kernel size adjustment (fine step size, interpolation, generation on the fly) may be more or less advantageous depending on the available hardware platform. Accordingly, the technique (or techniques) employed may be selected based on the hardware of the radiation detector system 100.

As discussed herein, each detector unit 110 of the illustrated embodiment includes a collimator 130. In some embodiments, the collimators 130 for each of the detector units 110 may be substantially similar. However, in some embodiments, different types of collimators may be employed. In some embodiments, at least one of the detector units 110 includes a first type of collimator 130a and at least one other of the detector units 110 includes a second type of collimator 130b. For example, the first type of collimator 130a may be a high-resolution collimator, and the second type of collimator 130b may be a high-sensitivity collimator. The processing unit 120 may then be configured to perform the convolutions based on collimator type. For example, the different collimator types may be differently modeled in the reconstruction.

In some embodiments, for example, the type of collimator used for each view may be recorded. Then, the reconstruction technique will employ n sets of convolution kernels, with n equal to the number of different types of collimators, and each set of kernels used for a given corresponding collimator type. Accordingly, during the convolution steps, the processing unit 120 may compute and/or fetch the appropriate kernel (or kernel set) for any given view based on the collimator used to acquire the particular view.

In various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, ASIC's and/or computers, which may be integrated in a common housing or unit, or which may distributed among various units or housings. It may be noted that operations performed by the processing unit 120 (e.g., operations corresponding to process flows or methods discussed herein, or aspects thereof) may be sufficiently complex that the operations may not be performed by a human being within a reasonable time period. For example, the forward projections and back projections discussed herein may rely on or utilize computations that may not be completed by a person within a reasonable time period.

In the illustrated embodiment, the processing unit 120 includes a memory 122. It may be noted that various aspects of the processing unit 120 described herein may be utilized in connection with various modules of the processing unit 120. Generally, the various aspects of the processing unit 120 act individually or cooperatively with other aspects to perform one or more aspects of the methods, steps, or processes discussed herein.

The memory 122 may include one or more computer readable storage media. The memory 122, for example, may store information describing the geometry of the system, predetermined kernels, or the like. Further, the process flows and/or flowcharts discussed herein (or aspects thereof) may represent one or more sets of instructions that are stored in the memory 122 for direction of operations of the radiation detection assembly 100.

It may be noted that while the processing unit 120 is depicted schematically in FIG. 1 as separate from the detector units 110, in various embodiments, one or more aspects of the processing unit 120 may be shared with the detector units 110, associated with the detector units 110, and/or disposed onboard the detector units 110. For example, in various embodiments, at least a portion of the processing unit 120 includes at least one application specific integrated circuit (ASIC) or field programmable gate array (FPGA) that is disposed onboard or integrated with the detector units 110.

Figure 4:
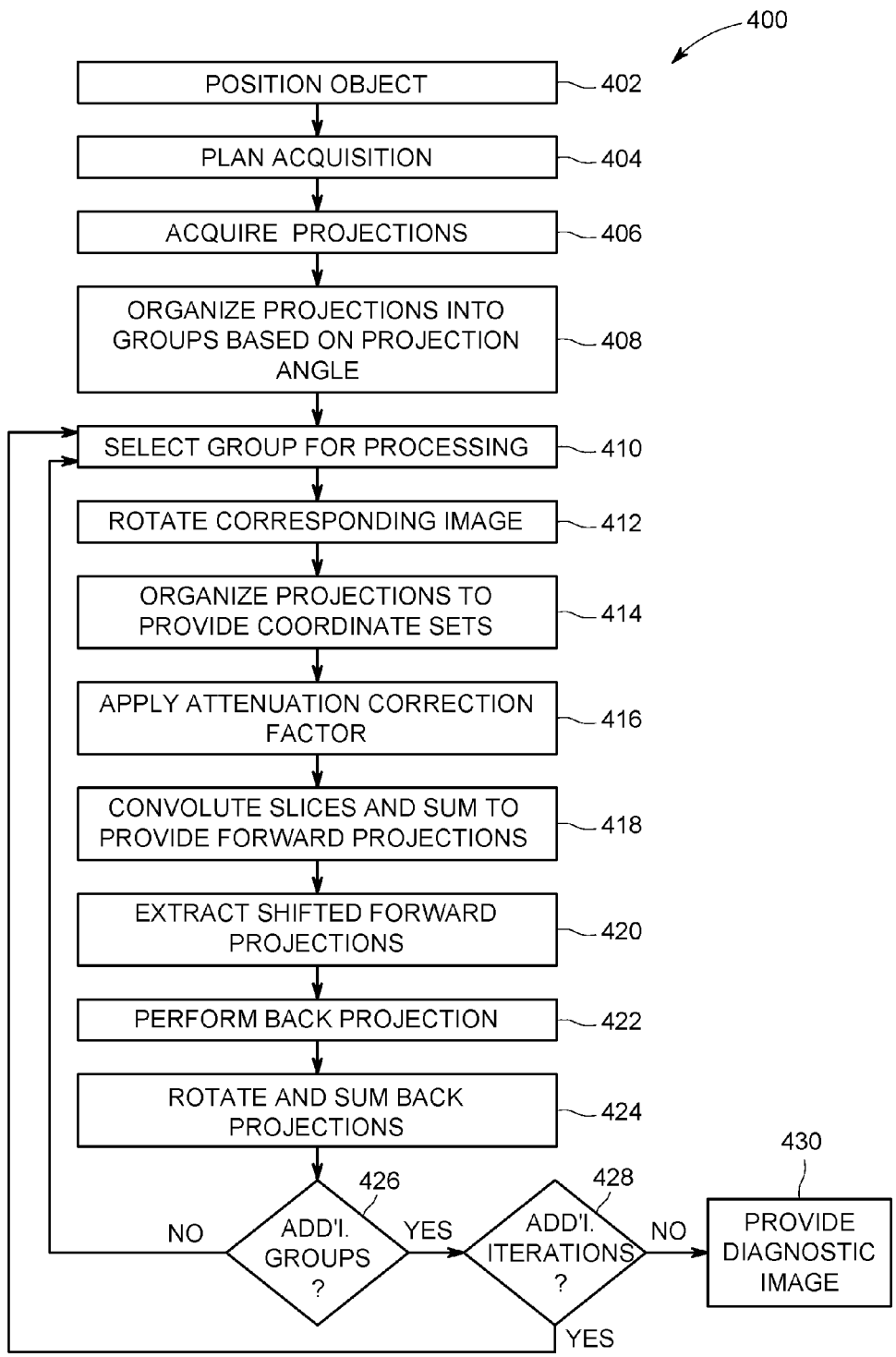
FIG. 4 shows a flowchart of a method, according to an embodiment.

FIG. 4 provides a flowchart of a method 400 for acquiring imaging information and reconstructing an image, in accordance with various embodiments. The method 400, for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be able to be used as one or more algorithms to direct hardware (e.g., one or more aspects of the processing unit 120) to perform one or more operations described herein.

At 402, an object (e.g., object 102) is positioned for imaging. For example, the object may be placed in the bore (e.g., bore 106) of a gantry (e.g., gantry 104) of an imaging system (e.g., radiation detector system 100). The object, for example, may be a human patient or a portion thereof that has been administered a radiopharmaceutical that causes emission of radiation from the object.

At 404, an acquisition is planned (e.g., by a processing unit such as processing unit 120). The planning of the acquisition, for example, may specify the positions and orientations of detector units to be used for acquiring imaging information of the object. For example, rotational positions based on rotations of a gantry may be specified, as well as positions throughout a sweep or pivot range as discussed herein. The various positions at which the detectors are positioned to acquire information may be identified by projection angle (e.g., angle with respect to predetermined axes and/or a predetermined orientation of the object). In various embodiments, the image acquisition may be planned to provide a predetermined number of projection angles. For example, the predetermined number of projection angles may be below a threshold (e.g., 360 or less).

At 406, projections are acquired. The projections include imaging information acquired at plural projection angles via plural detector units (e.g., detector units 110). In various embodiments, the detector units are disposed about a bore configured to accept the object to be imaged.

At 408, the projections are organized into groups based on the projection angles (e.g., the projection angles at which the projections were acquired). The groups may be organized by particular angles (e.g. "X degrees") or by range (e.g., X degrees+/−Y degrees). After being organized into groups, the groups may be separately processed (e.g., forward and back projected as part of an iterative process). Generally, in various embodiments, the groups are iteratively forward projected and back projected separately. It may be noted that, as discussed herein, various additional calculations may be performed between the forward and back projections.

In the illustrated embodiment, at 410 a group is selected for processing. In the illustrated embodiment, the groups are depicted as being processed serially; however, in various embodiments parallel processing may be employed to process groups separately but at the same time. It may be noted that before the actual processing at 410 there may be additional initializations (or preparations). For example, a calculation of the sensitivity map may be performed (e.g., for use as a scaling factor during the reconstruction). Other examples include reading the kernels and initializing data structures.

At 412, for the selected group, a corresponding image (e.g., an image corresponding to or formed using projections from the selected group but not other groups) is rotated. The image in the depicted embodiment is rotated from an original orientation (e.g., see FIG. 2) so that the group of projections are parallel to a first axis (e.g., x axis) of the rotated image (e.g., see FIG. 3).

At 414, the projections are organized based on a second axis coordinate (e.g., axis perpendicular to first axis or y axis) to provide coordinate sets. (As discussed herein, this step is optional). At 416, an attenuation correction factor may be applied to the projections. It may be noted that, as discussed herein, the timing of application of attenuation correction factor may vary among different embodiments, and may be specified by a determined attenuation correction parameter as discussed herein. It may be noted that attenuation correction factors may be applied before or after a forward projection convolution, and/or may be applied before or after a back projection convolution.

At 418, slices from each group (e.g., slices of each coordinate set) are convoluted and summed using kernels to provide a forward projection (e.g., a corresponding coordinate set forward projection). It may be noted that, in various embodiments, the kernels may be separable or one-dimensional kernels as discussed herein. Alternatively or additionally, the kernel distance may be adjusted from an original distance corresponding to a voxel size as discussed herein. It may be noted that, for embodiments utilizing detectors having different types of collimators, the convolutions may be performed based on collimator type (e.g., using kernels corresponding to particular collimator types).

At 420 of the illustrated embodiment, shifted forward projections are extracted. The forward projections may be shifted to account for the sweeping or pivoting of detector units as discussed herein.

At 422, a back projection is performed to provide back projections. For example, the back projection may include convoluting the coordinate set forward projections with a kernel, and summing the results onto xz slices. The back projection may also include shifting as discussed herein. As discussed herein, in various embodiments an error projection is calculated from the forward projection result and the measured projections (different algorithms for calculating the error projection may be utilized in different embodiments). The back projection may then be performed on the error projection, which is calculated based on the forward projection result, rather than being performed directly on the forward projection result.

At 424, the back projections are rotated back to the original orientation, and summed to provide a back projected transaxial image for the group. The back projected transaxial image may be used in subsequent iterations, or may be combined with images from other groups to provide a diagnostic image.

At 426 it is determined if any additional groups are to be processed (e.g., iteratively forward projected and back projected). If so, the method 400 proceeds to 410 and the next group (e.g., group of projections based on projection angle) is selected. If no additional groups are to be processed, the method proceeds to 428.

At 428 it is determined if additional iterations for the selected group are required. If so, the method 400 returns to 410. If no addition iterations for the selected group are required or desired, the method 400 proceeds to 430.

At 430, the resulting images from the separate processing of the groups are used (e.g., combined) to provide a final or diagnostic image that may be displayed or otherwise provided to a practitioner.

Figure 5:
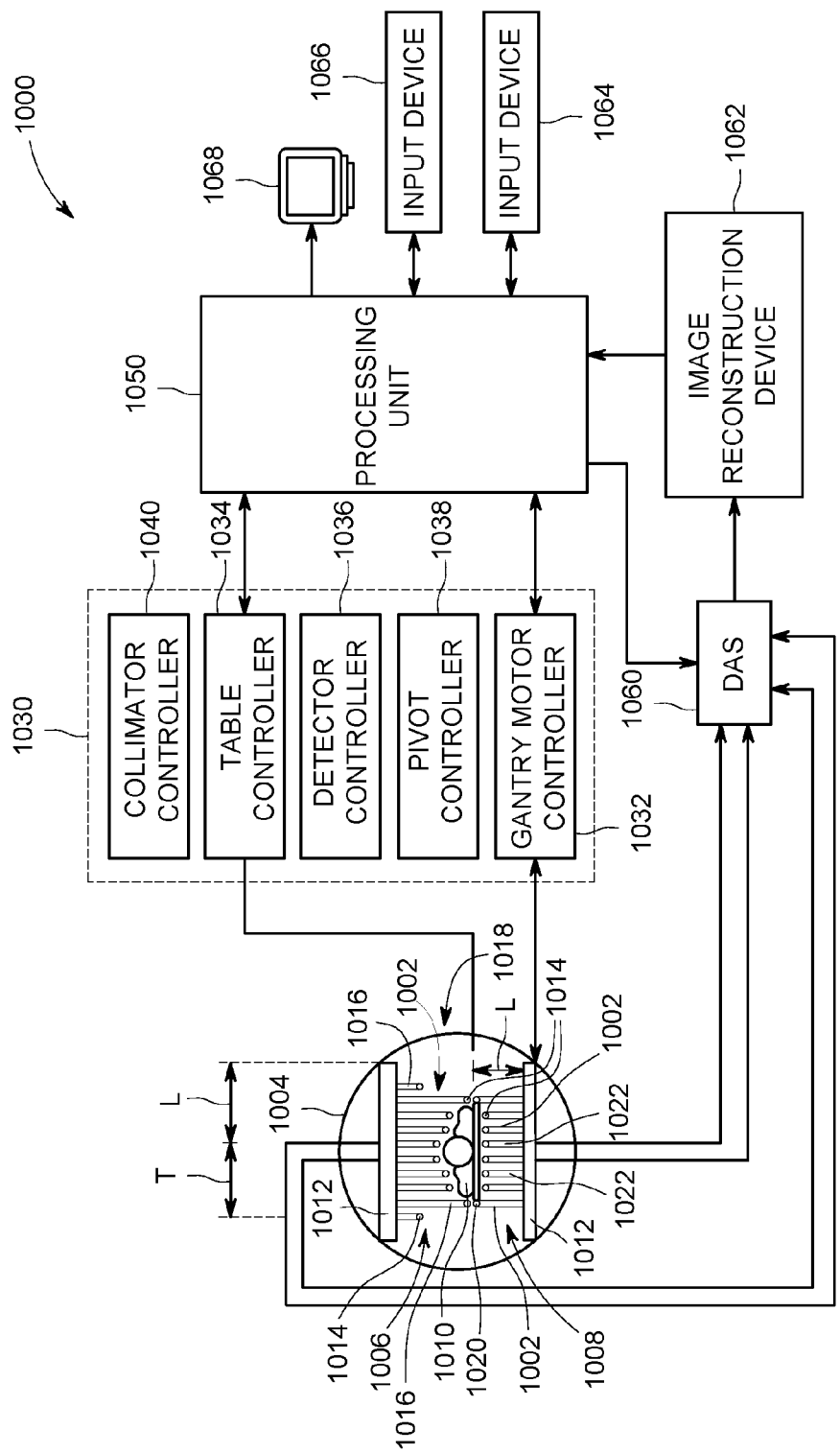
FIG. 5 shows a schematic view of an imaging system, according to an embodiment.

The embodiments described herein by FIGS. 1-4 may be implemented in medical imaging systems, such as, for example, SPECT, SPECT-CT, SPECT-MR, PET, PET-CT and PET-MR. Various methods and/or systems (and/or aspects thereof) described herein may be implemented using a medical imaging system. For example, FIG. 5 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 5 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 5. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 5). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 5 are depicted for ease of illustration as single collimators in each detector head. It may be noted that different types of collimators may be used in different columns. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 5). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 5 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation.

As used herein, the term "computer," "processor," or "module" may include any processor-based or microprocessor-based system including systems using microcontrollers, reduced instruction set computers (RISC), application specific integrated circuits (ASICs), field programmable gate arrays (FPGA's), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A radiation detector system comprising:
plural detector units disposed about a bore configured to accept an object to be imaged, each detector unit configured to acquire imaging information at plural corresponding projection angles; and
at least one processor operably coupled to the detector units, the at least one processor configured to:
acquire projections at the projection angles of the detector units;
organize the projections into groups based on the projection angles;
for each group of projections,
rotate a corresponding image from an original orientation so that the group of projections are parallel to a first axis of the rotated image,
convolute and sum slices from the group of projections using kernels to provide a forward projection;
perform a back projection to provide back projections; and
rotate the back projections to the original orientation and sum the rotated back projections to provide a back projected transaxial image.

2. The radiation detector system of claim 1, wherein the at least one processor is configured to apply a shift to register projection pixels with object voxels being imaged.

3. The radiation detector system of claim 1, wherein the at least one processor is configured to apply an attenuation correction factor.

4. The radiation detector system of claim 3, wherein the at least one processor is configured to determine an attenuation correction parameter corresponding to an application time of the attenuation correction factor.

5. The radiation detector system of claim 1, wherein the at least one processor is configured to modify a voxel size from an original size corresponding to a pixel size of the detector units.

6. The radiation detector system of claim 1, wherein the at least one processor is configured to use a first one-dimensional kernel for convolution in the first direction, and a second one-dimensional kernel for convolution in the second direction.

7. The radiation detector system of claim 1, wherein the at least one processor is configured to partition the acquired projections into subsets, and perform the forward and back projections based on the subsets.

8. The radiation detector system of claim 1, wherein the at least one processor is configured to plan image acquisition to provide a predetermined number of projection angles.

9. The radiation detector system of claim 1, wherein the at least one processor is configured to adjust a kernel distance from an original distance.

10. The radiation detector system of claim 1, wherein at least one of the detector units comprises a first type of collimator and at least one other of the detector units comprises a different, second type of collimator, wherein the at least one processor is configured to perform the convolutions based on collimator type.

11. A method comprising:
    acquiring projections of imaging information at plural projection angles via plural detector units disposed about a bore configured to accept an object to be imaged;
    organizing the projections into groups based on the projection angles; and
    for each group of projections,
        rotating a corresponding image from an original orientation so that the group of projections are parallel to a first axis of the rotated image;
        convoluting and summing slices of from the group of projections using kernels to provide a corresponding coordinate set forward projection;
        performing a back projection to provide back projections; and
        rotating the back projections to the original orientation and summing the rotated back projections to provide a back projected transaxial image.

12. The method of claim 11, further comprising applying a shift to register a projection with the object being imaged.

13. The method of claim 11, further comprising applying an attenuation correction factor.

14. The method of claim 13, further comprising determining attenuation correction parameter corresponding to an application time of the attenuation correction.

15. The method of claim 11, further comprising modifying a voxel size from an original size corresponding to a pixel size of the detector units.

16. The method of claim 11, further comprising using a first one-dimensional kernel for convolution in the first direction, and a second one-dimensional kernel for convolution in the second direction.

17. The method of claim 11, further comprising partitioning the acquired projections into subsets, and performing the forward and back projections based on the subsets.

18. The method of claim 11, further comprising planning the image acquisition to provide a predetermined number of projection angles.

19. The method of claim 11, further comprising adjusting a kernel distance from an original distance.

20. The method of claim 11, wherein at least one of the detector units includes a first type of collimator and at least one other of the detector units includes a different, second type of collimator, wherein the method further comprises performing the convolutions based on collimator type.

* * * * *